United States Patent [19]

Sheth et al.

[11] Patent Number: 5,348,748
[45] Date of Patent: Sep. 20, 1994

[54] PULSATILE ONCE-A-DAY DELIVERY SYSTEMS FOR MINOCYCLINE

[75] Inventors: Nitin V. Sheth, Middletown; Joseph J. Valorose, Jr., Montgomery, both of N.Y.; Keith A. Ellway, Shirrell Heath, United Kingdom; MaduraiGurusamy Ganesan, Suffern, N.Y.; Kieran G. Mooney, Whitstable, United Kingdom; Jerry B. Johnson, Upper Saddle River, N.J.

[73] Assignee: American Cyanamid Company, Wayne, N.J.

[21] Appl. No.: 81,632

[22] Filed: Jun. 23, 1993

Related U.S. Application Data

[62] Division of Ser. No. 844,109, Mar. 2, 1992, Pat. No. 5,262,173.

[51] Int. Cl.$^5$ .................. A61K 9/54; A61K 9/56; A61K 9/58
[52] U.S. Cl. .................. 424/494; 424/458; 424/461; 424/462; 424/490; 424/493; 424/495; 424/497; 424/498
[58] Field of Search ............... 424/458, 461, 462, 490, 424/493, 494, 495, 497, 498

[56] References Cited

U.S. PATENT DOCUMENTS

| | | | |
|---|---|---|---|
| 3,080,294 | 3/1963 | Shepard | 167/82 |
| 3,865,935 | 2/1975 | Amann | 424/181 |
| 4,138,475 | 2/1979 | McAnish et al. | 424/19 |
| 4,173,626 | 11/1979 | Dempski et al. | 424/19 |
| 4,250,166 | 2/1981 | Maekawa et al. | 424/81 |
| 4,353,887 | 10/1982 | Hess et al. | 424/15 |
| 4,606,909 | 8/1986 | Bechgaard et al. | 424/21 |
| 4,784,858 | 11/1988 | Ventouras | 424/468 |
| 4,808,413 | 2/1989 | Joshi et al. | 424/458 |
| 4,837,030 | 6/1989 | Valorose, Jr. et al. | 424/468 |
| 5,133,974 | 7/1992 | Paradissis et al. | 424/480 |
| 5,275,824 | 1/1994 | Carli et al. | 424/469 |
| 5,283,065 | 2/1994 | Doyon et al. | 424/468 |
| 5,286,497 | 2/1994 | Hendrickson et al. | 424/490 |

OTHER PUBLICATIONS

Abstract Japan Appln. No. 51-139712 and Japanese text.
Abstract Japan Appln. No. 62-226926 and Japanese text.

Primary Examiner—Thurman K. Page
Assistant Examiner—James M. Spear
Attorney, Agent, or Firm—James Costigan

[57] ABSTRACT

Pharmaceutical delivery systems containing 7-dimethyl-6-deoxy-6-demethyltetracycline or a non-toxic acid addition salt thereof comprising mixtures of a minor proportion of slow-release blended polymer coated spherical granules adapted to release part of the minocycline in a medium having a pH of below 3.9 and the rest in the range of from about 4.0 to about 7.5 and a major proportion of coated or uncoated quick-release granules adapted to release minocycline in a medium having a pH of less than about 3.9 and oral dosage unit form capsules containing the above are provided. These systems and formulations provide enhanced therapeutic blood levels of minocycline for at least about 24 hours when administered to a subject only once-a-day, regardless of whether the patient is fed or fasted. Methods for the preparation of the systems and formulations are provided as well.

24 Claims, 3 Drawing Sheets

PREPARATION OF SPHERICAL GRAUNULES

PREPARATION OF COATED SPHERICAL GRANULES

DRIED SPHERICAL GRANULES (FROM A)

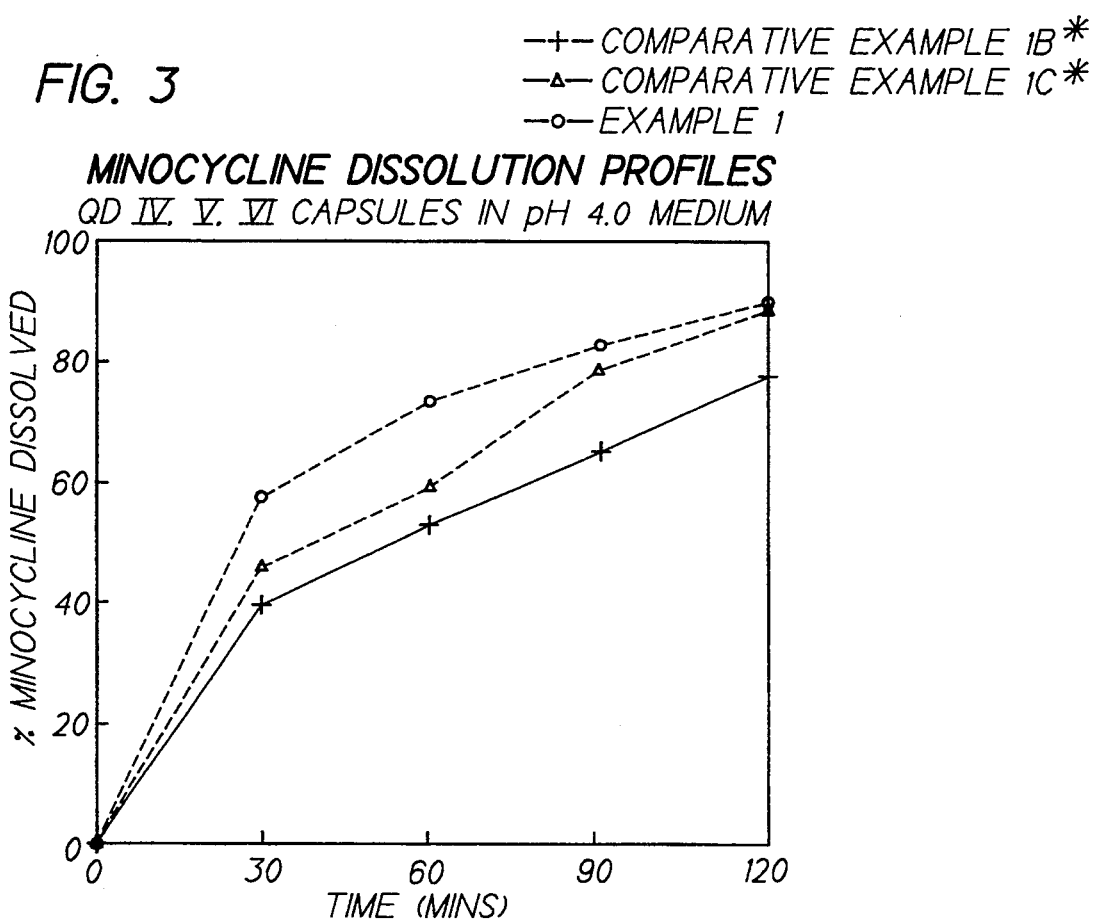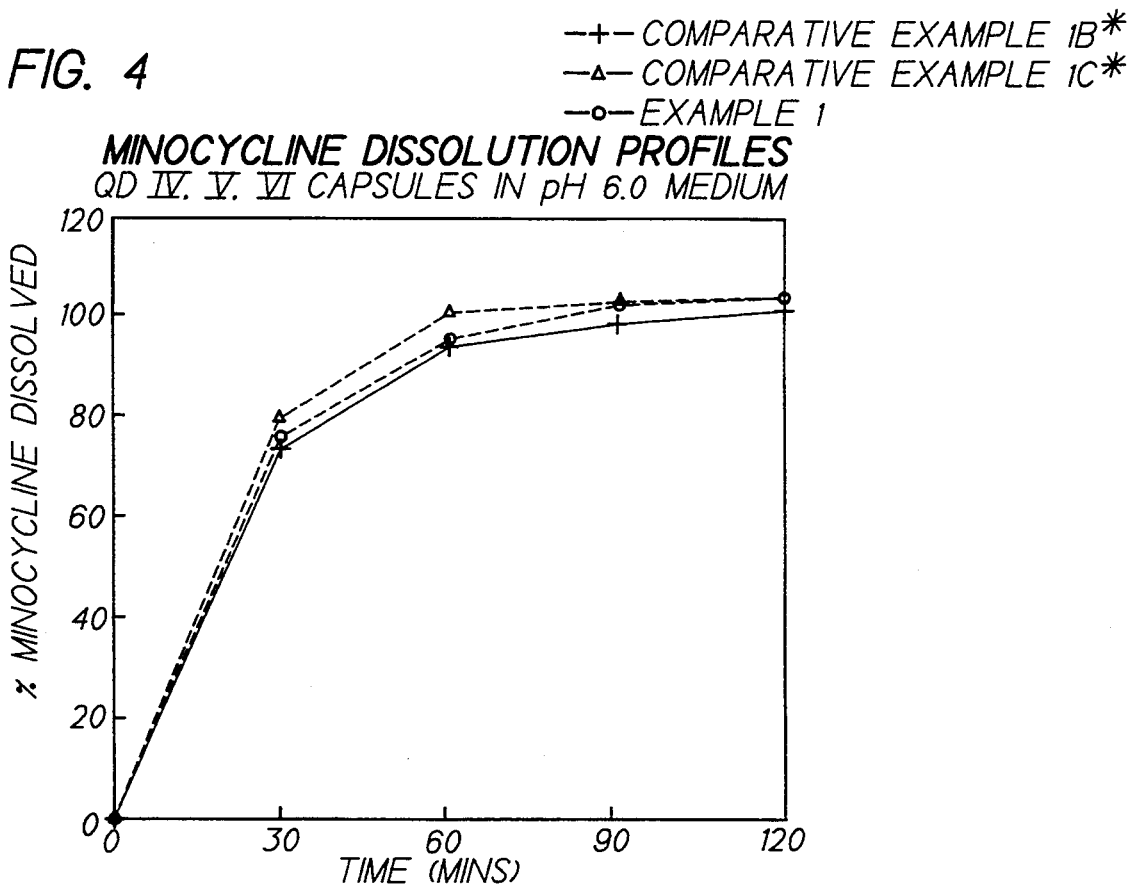

PULSATILE ONCE-A-DAY DELIVERY SYSTEMS FOR MINOCYCLINE

This is a divisional application, of application Ser. No. 07/844,109, filed Mar. 2, 1992, now U.S. Pat. No. 5,262,173.

FIELD OF THE INVENTION

The invention relates to pharmaceutical delivery systems for the prolonged controlled release of 7-dimethylamino-6-deoxy-6-demethyltetracycline (minocycline) or non-toxic acid addition salts thereof. It provides a once-a-day delivery system which maintains therapeutic blood level concentrations of the medicament in a patient for twenty-four hours by the once-a-day administration of improved custom designed formulations comprising a major proportion of an initial loading or first pulse of minocycline containing quick release granules and a minor proportion of a secondary loading or second pulse of minocycline containing blended pH-sensitive and pH-indifferent polymer coated spherical granules administered simultaneously. Spheronized pharmaceutical compositions comprising a major proportion of quick-release initial and a minor proportion of slow-release secondary minocycline loadings as well as oral dosage unit forms of all of the above are provided as well.

These pharmaceutical delivery systems, compositions and oral dosage unit forms, in comparison with those containing only a minor proportion of the initial quick-release loading of available minocycline, will provide more than 10% higher plasma level concentrations of minocycline in the therapeutic range for effective antibacterial activity for up to about twenty-four hours and they have the same excellent absorption characteristics regardless of whether they are administered to fed or fasting patients.

BACKGROUND OF THE INVENTION

The tetracycline compound, 7-dimethylamino-6-deoxy-6-demethyltetracycline, and its non-toxic acid addition salts are widely used in therapy primarily for their antimicrobial effects. Commonly assigned Boothe et al, U.S. Pat. No. 3,148,212, and Pesti et al, U.S. Pat. No. 3,226,436, describe the preparation of minocycline. Although the compounds have achieved widespread use in oral dosage forms, they have several drawbacks.

The minimum therapeutically effective blood serum or plasma concentration level of minocycline in a human subject varies according to the organism causing the infection. The concentration is determined in vivo by clinical evaluation and in vitro by microbiological assays. Currently, the minimum therapeutically effective concentration is believed to be in the range of from about 0.1 to about 1.0 mcg of minocycline/ml of serum.

Organisms currently known to be susceptible to minocycline therapy include a wide range of gram-negative and gram-positive bacteria including, but not limited to agents of rickettsiae (Rocky Mountain spotted fever, typhus fever and the typhus group, Q fever, rickettsial pox, tick fevers); Mycoplasma pneumonias (PPLO, Eaton agent); agents of psittacosis and ornithosis; agents of lymphogranuloma venereum and granuloma inguinale; the spirochetal agent of relapsing fever (*Borrelia recurrentis*); the agent of Lyme disease (*Borrelia burgdorfeni*), the agents of acne (*Propionibacterium Corynebacterium* acnes); the microorganisms *Haemophilus ducreyi* (chancroid), *Yersinia pestis* and *Francisella tularensis*, formerly *Pasteurella pestis* and *Pasteurella tularensis, Bartonella bacilliformis*, Bacteroides species, *Vibrio cormna* and *Vibrio fetus*, Brucella species, *Escherichia coli, Enterbacter aerogenes* (formerly *Aerobacter aerogenes*), Shigella species, Mima species, Herellea species, *Haemophilus influenzas* (respiratory infections), Klebsiella species (respiratory and urinary infections), many Streptococcus species including strains of *Streptococcus pyogenes* and *Streptococcus faecalis, Streptococcus pneumonias, Staphylococcus aureus* (skin and soft tissue infections), *Neisseria gonorrhoeae, Neisseria meningitidis, Treponema pallidum* and *Treponema pertenue* (syphilis and yaws), *Listeria monocytogenes*, Clostridium species, *Bacillus anthracis, Fusobacterium fusiforme* (Vincent's infection), Actinomyces species; and in the treatment of acute intestinal amebiasis and inclusion conjunctivitis. *Physician's Desk Reference*, 1987, Medical Economics Company, Oradell, N.J. (PDR 43rd Ed.).

Recent discovery shows that minocycline is absorbed at different rates in different portions of the gastrointestinal tract. Intubation studies in human patients have demonstrated that bioavailability of minocycline in the gastrointestinal tract, based upon 100 percent absorption in the stomach, is 106 percent in the duodenum, 80 percent in the jejunum and 58 percent in the ileum, indicating that minocycline demonstrates reduced absorption in the lower gastrointestinal tract.

The human stomach empties in about one hour in a fasting subject and in about one to about four hours with food. The half life of minocycline when taken without food is approximately 10 hours. When taken with food, the half life is extended to approximately 14 to 16 hours.

It has not been possible to achieve a once-a-day therapeutic blood level of minocycline using only delayed release granules of minocycline with or without food ingestion. Traditional pharmaceutical forms containing minocycline require frequent ingestion of multiple doses per day resulting in wide variations in serum concentration throughout the course of treatment and in poor patient compliance and traditional delayed release forms containing minocycline are incompletely absorbed in the gastrointestinal tract. This indicates a need for a custom designed once-a-day delivery system for minocycline to provide optimal therapeutic effect and patient compliance.

Lederle Laboratories has recently offered for use by the medical profession, capsules under the trademark MINOCIN® containing specially coated pellets of minocycline hydrochloride for oral administration. See, PDR 44th Ed. (Pages 1168–1170). In contrast to tablets and powder-filled capsules, pelletized minocycline hydrochloride provides virtually complete absorption with dairy products and food. The capsules, however, are not intended to provide a once-a-day dosage form.

Valorose et al, U.S. Pat. No. 4,837,030, disclose hard gelatin or soft gelatin capsules filled with minocycline comprising spherical granules. This patent teaches controlled release formulations of minocycline wherein the rate of release in the stomach and intestines is controlled. The delivery system may be comprised of coated or uncoated spheres. The medicament may be within the sphere or in the coating. Valorose further teaches coating the spherical granules with hydroxypropyl methylcellulose and hydroxypropyl methylcellulose phthalate. The controlled release in Valorose, however, is not taught to be prolonged up to 24 hours.

Shepard, U.S. Pat. No. 3,080,294, discloses a sustained release pharmaceutical tablet comprising an inner core coated with multiple layers of an active medicament mixture, each layer releasing a portion of active medicament as it is successively dissolved. Such layers are not pH adapted, however. Shepard further teaches sustained release pharmaceutical formulations wherein medicament coated pellets and uncoated medicament pellets maintain therapeutic blood concentration levels for prolonged periods of time. The medicament may be in the coating or in the core. Shepard also teaches the use of coatings comprised of cellulose esters and pH sensitive polymer coatings. As explained in example 4 of Shepard, the dosage forms are formulated so that a predetermined amount of active ingredient may be released in the stomach (pH less than 3.9) and a predetermined amount may be released in the intestines (pH 4-7.5) approximately.

In copending, commonly assigned U.S. patent application, Ser. No. 07/410,708, filed Sep. 21, 1989, now abandoned it is disclosed that a specific minocycline composition can be formulated to provide at least minimum therapeutic serum levels of the minocycline in a human subject for about 24 hours through once-a-day two pulse administration systems, comprising an initial loading component providing the first pulse which is absorbed up to 100 percent in the stomach and a secondary loading component providing the second pulse which is absorbed up to 100 percent in the duodenum and the upper part of the small intestine. Working examples are provided which contain a minor proportion of the initial loading component and a major proportion of the secondary loading component. In addition, the working examples include procedures to coat granules comprising the secondary loading component with a blended polymer coating composition to give them slow release characteristics. The formulations of the copending application are taught to be processable into capsule oral dosage unit forms. In vivo data with a preferred embodiment of the copending application comprising capsules containing 46% of the total dose in the form of uncoated quick-release pellets and 54% in the form of single polymer (hydroxypropyl methylcellulose phthalate)-coated slow-release pellets showed good bioavailability over 24 hours after a single administration, approaching the achieved with two divided doses of conventional minocycline tablets.

It has now been discovered that bioavailability can be even more improved by increasing the ratio of quick release initial loading pellets to slow release secondary loading coated pellets and by using a modified coating composition for the latter. Thus, for example, the bioavailability can be improved by greater than 10% by using a major proportion, e.g., 60% of the quick-release granules and a minor proportion, e.g., of the slow-release granules and providing the latter with a coating comprising a small amount of water-soluble polymer in the pH-sensitive polymer previously used alone. In addition, in multidose studies, the mixed pellet dosage forms of the present invention exhibit a surprising retention of bioavailability after ingestion of food in comparison with tablets employed in the present state of the art. Data are presented hereinafter which show that fed subjects had an absorption of 100% of that of the fasted subjects with the dosage forms of this invention but only 90.6% with the prior art tablets.

These results are surprising because just the opposite would be expected. An early release of most of the minocycline in the stomach should reduce the long time effectiveness, but, as will be seen, single dose bioavailability versus the reference tablet given twice a day is increased from 79% to 89%, and the latter is unaffected by food intake as is shown in the multidose studies.

BRIEF DESCRIPTION OF THE DRAWINGS

FIG. 3 is a graphic illustration of the release rate of minocycline from blended polymer coated spherical granules of this invention in comparison with those not of this invention in a medium having a pH of about 4.0.

FIG. 4 is a graphic illustration of the release rate of minocycline hydrochloride from blended polymer coated spherical granules as in FIG. 3 but in a medium having a pH of 6.0.

SUMMARY OF THE INVENTION

Figure 1:
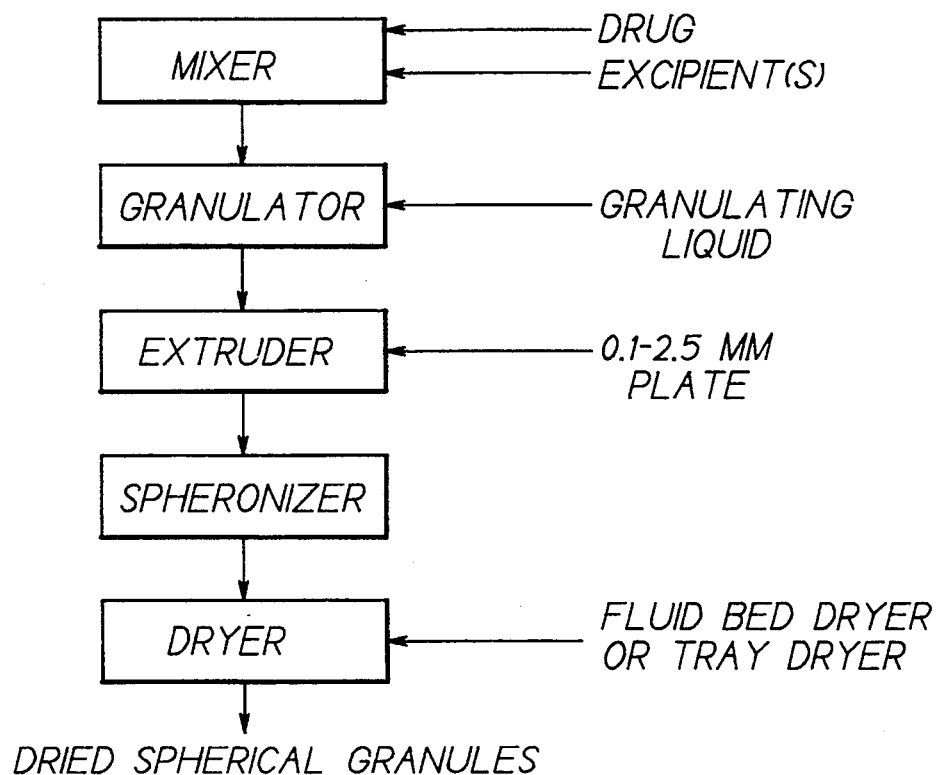
FIG. 1 is a graphic illustration of a method for the production of uncoated quick release granules and precursors of blended polymer coated spherical granules according to the present invention.

According to the present invention, there are provided improved pharmaceutical delivery systems adapted to provide a therapeutically effective blood concentration levels of 7-dimethylamino-6-deoxy-6-demethyltetracycline or a non-toxic acid addition salt thereof for a sustained period of time of up to about twenty-four hours comprising:

(A) from 51 to 80 parts by weight per 100 parts by weight of (A) and (B) combined of an initial loading therapeutically effective number of quick release granules which comprise
  (a) (i) an effective amount of at least one pharmaceutically acceptable excipient; and
  (ii) an effective antibacterial amount of 7-dimethylamino-6-deoxy-6-demethyltetracycline or a non-toxic acid addition salt thereof, on or in said quick release granules;
said quick release granules being adapted to release substantially completely said tetracycline or salt thereof in a medium having a pH of less than about 3.9; and (B) from 20 to 49 parts by weight per 100 parts by weight of (A) and (B) combined of a secondary loading therapeutically effective number of blended polymer coated spherical granules which comprise
  (a) (i) an independent effective amount of at least one pharmaceutically acceptable excipient which may be the same as or different than (A)-(a)(i); and
  (ii) an independent effective antibacterial amount of 7-dimethylamino-6-deoxy-6-demethyltetracycline or a non-toxic acid addition salt thereof, on or in said coated spherical granules; and
  (b) a substantially uniform coating comprising a blend of at least two polymers on said coated spherical granules (B) one of which is non pH-sensitive and rapidly erodible in water and the other of which is pH-sensitive and erodible in a medium having a pH in the range of from about 4.5 to about 6.5; said coated spherical granules thereby being adapted to release some of said tetracycline or salt thereof in a medium having a pH in the range of from about 1.0 to about 3.0 and the remainder rapidly in a medium having a pH in the range of from about 4.5 to about 6.5.

Preferred features of the invention are such pharmaceutical delivery systems in which the quick release granules (A) comprise from about 55 to about 70 parts by weight and the coated granules (B) comprise from about 20 to about 45 parts by weight per 100 parts by weight of (A) and (B) together, and especially those wherein the quick release granules (A) comprise about 60 parts by weight and the coated granules (B) comprise about 40 parts by weight per 100 parts by weight of (A) and (B) together.

The invention further contemplates oral dosage units in the form of pharmaceutically acceptable liquid carriers containing the above compositions or systems, hard or soft shell capsules at least partially filled with the above compositions or systems, and tablets formed from the above compositions or systems.

The invention also provides methods of maintaining a therapeutic level of the tetracycline or salt thereof in the blood stream of a warm-blooded mammal for about 24 hours comprising administering to the mammal the pharmaceutical delivery systems or oral dosage units above.

A method for the preparation of a pharmaceutical delivery system is provided comprising the steps of:
(I) forming an initial loading component by
  (a) blending
    (i) an effective amount of at least one pharmaceutical acceptable excipient; and
    (ii) an effective antibacterial amount of 7-dimethylamino-6-deoxy-6-demethyltetracycline or a non-toxic acid addition salt thereof;
  (b) granulating the resultant blend in the presence of a granulating liquid;
  (c) extruding the resultant granulate;
  (d) spheronizing the resultant extrudate to form quick release granules which are adapted to release substantially completely said tetracycline or salt thereof in a medium having a pH of less than about 3.9; and
  (e) drying said quick release granules; and
(II) forming a secondary loading component by
  (a) blending
    (i) an independent amount of at least one pharmaceutical acceptable excipient which may be the same as or different than (A)(a)(i); and
    (ii) an independent effective antibacterial amount of 7-dimethylamino-6-deoxy-6-demethyltetracycline or a non-toxic acid addition salt thereof;
  (b) granulating the resultant blend in the presence of a granulating liquid;
  (c) extruding the resultant granulate;
  (d) spheronizing the resultant extrudate to form precursors of coated spherical granules;
  (e) drying said precursors;
  (f) coating said precursors with a substantially uniform coating comprising a blend of at least two polymers, one of which is non pH-sensitive and rapidly erodable in water and the other of which is pH-sensitive and erodible in a medium having a pH in the range of from about 4.5 to about 6.5 and
(B) preparing therefrom a controlled release pharmaceutical composition in oral dosage unit form by the step of at least partially filling a hard or a soft shell capsule with a pharmaceutical delivery system with from about 51 to about 80 parts by weight of the quick release granules prepared by steps (I) and from about 20 to about 49 parts by weight of the slow release granules produced by the steps (II) and optionally sealing said capsules.

Preferred features of the invention comprise such a method wherein the capsule is filled with from about 55 to about 70 parts by weight of the quick release granules prepared by steps (I) and from about 30 to about 45 parts by weight of the coated granules prepared by steps (II), per 100 parts by weight of said granules and especially preferred is such a method wherein the capsule is filled with about 60 parts by weight of the quick release granules prepared by steps (I) and about 40 parts by weight of the coated granules prepared by steps (II), per 100 parts by weight of the granules.

The pharmaceutical delivery systems and the capsule oral dosage unit forms described above provide once-a-day prolonged effect controlled release forms of minocycline which maintain improved therapeutic blood levels for periods of up to twenty-four hours resulting in desirable and effective antibacterial therapy and less frequent administration to a subject. They also avoid high local concentrations in a system which may cause side effects such as gastroirritability.

DETAILED DESCRIPTION OF THE INVENTION

Novel pharmaceutical delivery systems have been discovered comprising mixed blends of an initial loading therapeutically effective number of quick-release granules and a secondary loading therapeutically effective number of blended polymer coated spherical granules. These systems and compositions can be filled into capsules to prepare oral dosage units. Many benefits can be realized from these novel delivery systems and oral dosage unit forms over conventional controlled release formulations. They result in a superior controlled and prolonged delivery of minocycline to a subject which in turn results in the achievment of once-a-day dosages of 7-dimethylamino-6-deoxy-6-demethyltetracycline or non-toxic acid addition salts thereof in the compositions and oral dosage unit forms to sustain a desired blood level concentration in a subject for a relatively long period of time of up to twenty-four hours. Therefore, less frequent administration of the minocycline compound to a subject, possibly fewer and lessened side effects, including reduced gastroirritability, and better subject compliance with a medicament regimen are possible.

Oral dosage unit forms are those which are orally administered and contain medicaments which are absorbed into the blood stream from the alimentary tract.

An initial loading therapeutically effective amount or number of quick release granules is that amount or number which provides an immediate or rapid and substantially complete release in a medium having a pH of less than about 3.9 and, preferably in a range of from about 1.0 to about 2.5, such as in the human stomach and thereby delivers and maintains a recommended dosage or concentration level of 7-dimethyamino-6-deoxy-6-demethytetracycline or a non-toxic acid addition salt thereof to the blood stream or plasma of a subject within a recommended period of time and maintains that level or a further recommended level for a further recommended period of time. This provides a first pulse of minocycline, preferably in the stomach, which quickly attains therapeutic plasma drug levels, i.e. at least that amount determined by in vivo clinical evaluation or in vitro microbiological assay to treat successfully infections caused by the invading organism or organisms.

A secondary loading therapeutically effective amount or number of blended polymer coated spherical granules is that amount or number which provides a slow release of a small amount in the stomach and a complete release in a medium having a pH in the range of from about 4.0 to about 7.5 and preferably from about 4.0 to about 6, as in the human upper intestinal tract and particularly in the duodenum/jejunem. The use of a higher level of quick release granules in proportion to delayed release granules is believed to result in a higher absorption of minocycline because minocycline is preferentially absorbed in the duodenum and jejunem. It thereby delivers and maintains a further recommended dosage or concentration level of 7-dimethylamino-6-deoxy-6-demethyltetracycline or a non-toxic acid addition salt thereof to the blood stream or plasma of a subject within an independent recommended period of time and maintains that level or a different recommended level for an independent additional recommended period of time. This second pulse provides a delayed release and a controlled release of minocycline, preferably in the duodenum, which extends therapeutic plasma drug levels initially achieved by the first pulse, i.e. at least that amount determined effective for the particular organism causing the infection as described above, for a total prolonged period of time, i.e. up to about 24 hours.

The initial loading of the minocycline is achieved by the administration of quick release granules containing the minocycline. The secondary loading can mixed blends of initial loading and secondary loading components. The total period of time this therapeutic plasma drug level is maintained from the combined effect of the two different types of granules is preferably about 24 hours. Therefore, only one dosage unit will provide effective antimicrobial therapy for an entire day, the total therapeutic amount, i.e. the initial loading therapeutically effective amount or number plus the secondary loading therapeutically effective number, being that amount and/or number which will achieve and will maintain at least a therapeutically effective concentration of 7-dimethylamino-6-deoxy-6-demethyltetracycline or a non-toxic acid addition salt thereof/ml of serum or plasma in the blood serum or plasma of a human subject for about 24 hours.

The salts of minocycline useful in the present invention are the non-toxic acid addition salts, e.g. sulfonic, trichloroacetic, hydrochloric acid salts.

The last named compound is also known as minocycline hydrochloride. Typically, minocycline hydrochloride has been administered orally in a daily dosage of about 100 to about 400 mg in at least two and often more divided doses a day in a normal adult human being. It is commercially available in many forms under the trademark Minocin from Lederle Laboratories, Wayne, N.J. (PDR 44th Ed.).

It should additionally be noted that minocycline hydrochloride readily undergoes epimerization and oxidative degradation to epiminocycline, a pharmacologically inactive and undesirable tetracycline compound. The amount of the epimer should be minimal but may range as high as from about 1.5 percent to about 10 percent without affecting the intended once daily dose of the present invention.

Preferably, the pharmaceutical delivery systems and oral dosage unit forms of the present invention will contain from about 25 mg to about 400 mg of 7-dimethylamino-6-deoxy-6-demethyltetracycline or non-toxic acid addition salt thereof and most preferably from about 80 mg to about 280 mg. The ratio of initial loading component, i.e. minocycline powder, quick release granules, quick release coating or the like, to the secondary loading component, i.e. blended polymer-coated spherical granules or single coated core, ranges from about 51:80 to about 20:49 parts by weight of initial loading component and secondary loading component combined and preferably from about 55:70 to about 30:45. Preferably, the initial loading component, the secondary loading component, or both independently contain from about 20 to about 200 mg of minocycline.

The rapid and substantially complete release of the initial loading component is such that the initial loading component releases greater than about 70 percent and preferably greater than about 80 percent of the minocycline in less than about 90 minutes and preferably less than about 60 minutes in a medium of aqueous buffer, e.g. hydrochloric acid and/or acetate buffer, having a pH of less than about 3.9. Therefore, any optional polymer coating on the initial loading component must be specifically rapidly and substantially erodible or dissolvable to permit the initial loading component to meet these conditions.

The rapid and substantially complete release of the secondary loading component core is such that the secondary loading component or single coated core releases greater than about 40 percent and preferably greater than about 70 percent of the minocycline in less than about 90 minutes in a medium of aqueous buffer, e.g. acetate and/or phosphate buffer, having a pH in the range of from about 4.5 to about 6.5. Therefore, the blended polymer coating must be both partially water-soluble and thereafter specifically rapidly and substantially completely erodible or dissolvable at the specified pH range to permit the secondary loading component to meet these conditions.

Further preferred embodiments of the present invention provide additionally that either from about 5 to about 20 percent of the minocycline in the secondary loading component is released in about 2 hours when suspended in a medium of simulated gastric fluid having a pH of about 1.2 at about 37° C. or from about 20 to about 50 percent of the minocycline in the secondary loading component is released in about 2 hours when suspended in a medium of simulated gastric fluid having a pH of about 1.2 at about 37° C.

The drug is released when it may be determined by a standard assay.

Many pharmaceutical excipients will be suitable for use in this invention. Judicious selection will be easy with the requirements and the test procedures mentioned herein kept in mind. An excipient with a known degree of solubility in water and solubility and swellability in the respective juices of the stomach and the upper small intestine, particularly the duodenum, should be used. Such excipients in either the quick release granules, the slow release blended polymer coated spherical granules, or a combination of any of the foregoing include lactose, other mono- or di-saccharides, microcrystalline cellulose, starch, sodium carboxymethyl cellulose, hydroxypropyl cellulose, hydroxyethyl cellulose, crosscarmellose sodium, pregelatinized starch, polyvinylpyrrolidone, cross-linked polyvinylpyrrolidone, hydroxypropyl methylcellulose, cellulose acetate, hydroxypropyl methylcellulose phthalate, polyvinyl acetate phthalate, microcrystalline cellulose in combination with lactose, microcrystalline cellulose in combination with sodium carboxymethyl cellulose, microcrystalline cellulose in combination with crosscarmellose sodium, mixtures of any of the foregoing and the like as well as others with which those of ordinary skill in the art will be familiar, most of which are listed in standard references, for example, *Remington's Pharmaceutical Sciences*, 1985, 17th Edition, Philadelphia College of Pharmacy and Science, Chapter 68, Pharmaceutical Necessities, pages 1278–1320.

Although a single excipient can be used, e.g., microcrystalline cellulose, desirable results may require more care in selecting an appropriate amount of minocycline to be used in the spheres. Therefore, combinations of more than one excipient may be desirable.

Suitable forms of microcrystalline cellulose are, for example, the materials sold as Avicel ® PH-101 and Avicel ® PH-105 (available from FMC Corporation—American Viscose Division, Avicel Sales, Marcus Hook, Pa., U.S.A.). Avicel ® PH-101 is characterized as having an average particle size of 50 um, particle size specification of +60 mesh less than 1 percent and +200 mesh less than or equal to 30.0 percent, moisture specification of less than 5.0 percent and acceptable flow properties. Avicel ® PH-105 is characterized as having an average particle size of 20 um, particle size specification of +400 mesh less than or equal to 1.0 percent, moisture specification of less than 5.0 percent, and poor flow properties.

A suitable mixture of microcrystalline cellulose and sodium carboxymethyl cellulose is, for example, the material sold as Avicel ® RC-581 by FMC Corporation. Avicel ® RC-581 is characterized as having an average particle size of less than 0.2 micron, particle size specification of 60 mesh less than or equal to 0.1 percent, and moisture specification of less than 6 percent.

The term "spheres" is well known in the pharmaceutical art, and means spherical granules having a diameter in the range of from about 0.1 to about 2.5 millimeters, preferably from about 0.5 to about 2 millimeters, and most preferably from about 0.8 to about 1.5 millimeters. Preferably, the quick release granules are spherical as well. If spheres having the medicament as a surface layer are to be prepared, coated seeds, e.g., non-pareil seeds or sugar crystals, may be used. Such non-pareil seeds are generally of about 0.1 mm to about 2.0 mm in size and typically are about 1.0 millimeter in size. They can comprise, for example, a blend of sugar and starch. Such crystals are generally 0.01 mm to about 0.1 mm in size. The cores of the multi-coated composition are preferably such seeds. However, the cores may comprise minocycline alone or in combination with the excipient as well.

The quick release granules typically are uncoated. However, they may be optionally coated with a polymer coating which is rapidly and substantially completely erodible in a medium having a pH of less than about 3.9 and particularly in the human stomach, thereby leaving their immediate or quick release characteristics relatively unchanged.

The film forming polymer, if used, can vary widely in type and amount which correlates into film or coating thickness. Illustrative but not limiting quick release spherical granule coating polymers are methyl cellulose, ethylcellulose, hydroxyethyl cellulose, hydroxypropyl cellulose, hydroxypropyl methylcellulose, hydroxypropyl methylcellulose phthalate, cellulose acetate phthalate, hydroxypropyl methylcellulose succinate, polymers and copolymers of (meth)acrylic acid or (meth)acrylic acid methyl ester, polyvinyl acetate phthalate or polymers or copolymers of polyvinyl acetate, cellulose acetate, fatty acids and esters thereof, cellulose acetate trimellitate, and mixtures of any of the foregoing, adapted to substantially completely dissolve in a medium having a pH of less than about 3.9. The coatings can include conventional additives, such as plasticizers, pigments, colorants, etc. The plasticizers include mineral oil, high boiling esters, vegetable oils and the like.

Commercial coating compositions found to be useful include Eudragit ®, a product of Rohm Pharma, Westerstadt, Germany, which comprises an anionic polymerizate of methyacrylic acid and methyl methacrylate; Surelease ® a product of Colorcon, Inc., West Point, Pa., which comprises an aqueous dispersion of ethylcellulose, dibutyl sebacate, oleic acid, fumed silica, and ammonium hydroxide; Aquacoat ®, a product of FMC Corp., which comprises an aqueous dispersion of ethylcellulose; Coateric ®, a product of Colorcon, Inc., which comprises polyvinyl acetate phthalate; Aquateric ®, a product of FMC Corp., which comprises cellulose acetate phthalate; Eastman C-A-P ™, a product of Eastman Kodak Company, Rochester, N.Y., which comprises cellulose acetate phthalate; and Eastman C-A-T ™, a product of Eastman Kodak Company, which comprises cellulose acetate trimellitate. Preferred as a coating material for the quick release granules is hydroxypropyl methylcellulose.

Although up to about 1 to about 10 parts by weight gain due to the coating based upon the weight of the uncoated quick release granules is suitable, from about 2 to about 5 parts by weight gain is preferred and about 2 parts by weight gain is most preferred.

This polymer coating may also optionally include a precoat, an overcoat or a combination of the foregoing. For best results, a 1 to 10 parts by weight gain level is preferred in addition to the standard coating when using aqueous coating formulations.

The polymer coating of the coated spherical granules is blended to provide solubility characteristics which are independent of pH and also pH sensitive. The coating should be capable of beginning to swell and slowly release minocycline in the stomach. Upon reaching the duodenum/jejunem, the pH-sensitive polymer dissolves, and minocycline is completely released from the coated pellets and is rapidly and substantially completely erodible because the medium has a pH in the range of from about 4.0 to about 7.5, whereby erosion is inhibited but not precluded by a pH outside that range such as in the human stomach. Thus there is a rapid, controlled release of the remainder of the medicament from the coated spherical granules in the upper small intestine, i.e. duodenum.

The film forming polymers can vary widely in type and amount which correlate to film or coating thickness.

Illustrative but not limiting polymers for coating the pellets are methylcellulose, ethylcellulose, hydroxyethyl cellulose, hydroxypropyl cellulose, hydroxypropyl methylcellulose, hydroxypropyl methylcellulose phthalate, cellulose acetate phthalate, hydroxypropyl methylcellulose succinate, a polymer or copolymer of (meth)acrylic acid or (meth)acrylic acid methyl ester, polyvinyl acetate phthalate or polymers or copolymers of polyvinyl acetate, cellulose acetate, fatty acids and esters thereof, cellulose acetate trimellitate, and mixtures of any of the foregoing. These coatings can include any of the conventional coating additives from above as well. A suitable form of hydroxypropyl methylcellulose is one having a viscosity in the range of 3 to 100 cps at 200C (U.S. National Formulary XIII), and more particularly a viscosity of 6 cps at 20° C. Preferred as the coating is a combination of hydroxypropyl methylcellulose phthalate and hydroxypropyl methylcellulose, and most preferably, these coatings will be adapted to dissolve substantially completely in a medium having a pH of about 5.0 or greater than about 5.5.

Although from about 5 to about 35 parts by weight gain due to the blended polymer coating based upon the weight of the uncoated spherical granules (precursors of coated spherical granules) or core is suitable, from about 5 to about 25 parts by weight gain is preferred and from about 10 to about 25 parts by weight is most preferred.

The polymer coating may also independently include a precoat, an overcoat, or a combination of the foregoing. For best results, a 1 to 10 parts by weight gain level is preferred in addition to the standard coating when using an aqueous formulation.

The amounts of minocycline and excipient which comprise the quick release granules can vary broadly but will usually be in the range of from about 10 to about 70 parts by weight of minocycline and from about 90 to about 30 parts by weight of excipient based upon 100 parts by weight of minocycline and excipient combined. Preferably, the quick release granules comprise about 50 parts by weight of minocycline and about 50 parts by weight of excipient based upon 100 parts by weight of minocycline and excipient combined.

The amounts of minocycline and excipient which comprise the precursors of the blended polymer coated spherical granules or the core of the multicoated compositions should be in the range of from about 10 to about 80 parts by weight of minocycline and from about 90 to about 20 parts by weight of excipient based upon 100 parts by weight of minocycline and excipient combined. The amount of blended polymer coating on the precursors or the core varies broadly as well and is described above. Preferably, the coated spherical granules will comprise about 60 parts by weight of minocycline and about 40 parts by weight of excipient based upon 100 parts by weight of minocycline and excipient combined, and the blended polymer coating will comprise a weight gain of about 10 to about 25 parts by weight based upon 100 parts by weight of minocycline and excipient combined.

The components of the pharmaceutical delivery systems be filled into either hard shell gelatin or soft shell gelatin capsules alone or with additional active medicaments, lubricants, disintegrants, plasticizers, colorants, pigments, flavoring, additional excipients or a combination of any of the foregoing by any conventional capsule forming and/or filling machine and optionally may be sealed by any means commonly known to one of ordinary skill in the pharmaceutical arts including but not limited to spot-welding, gelatin bands and matched locking rings.

The hard shell capsules used in the present invention are generally comprised of gelatin, water and optionally, FD&C colorants, opacifying agents such as titanium oxide, sulfur dioxide to prevent any decomposition or a combination of any of the foregoing. They generally comprise two sections, one slipping over the other, completely surrounding the filling.

The soft shell capsules used in the present invention are generally a soft, globular, gelatin shell somewhat thicker than the shell of the hard shell capsule. The gelatin is usually plasticized by the addition of glycerin, sorbitol, or a similar polyol. They may also contain a preservative to prevent the growth of fungi.

All of the pharmaceutical delivery systems, compositions or oral dosage unit forms of the present invention can be prepared using any conventional pharmaceutical production equipment.

FIG. 1 illustrates the typical steps in the preparation of uncoated spherical granules for use as either uncoated quick release granules or as precursors of pH sensitive polymer coated spherical granules. Firstly, an effective amount of at least one pharmaceutically acceptable excipient and an effective antibacterial amount of 7-dimethylamino-6-deoxy-6-demethyltetracycline or a non-toxic acid addition salt thereof are blended in a mixer. The resultant blend of the first step is granulated with a liquid medium, e.g. an aqueous solution or an organic solvent and preferably water, until the proper consistency for extrusion is realized. The resultant granulated mass is then extruded in an extruder or extruder/spheronizer, through a suitably sized, e.g. 1.0 mm, perforated plate and is spheronized at high speed for a time sufficient to form spherical granules. The wet spherical granules are then dried in conventional equipment at suitable temperatures, e.g. such as tray dryers at 55° to 65° C. or a conventional fluid bed dryer system at 65° to 70° C. to a low moisture level, e.g. about 1 to about 7 percent and preferably about 2 to about 5 percent.

Figure 2:
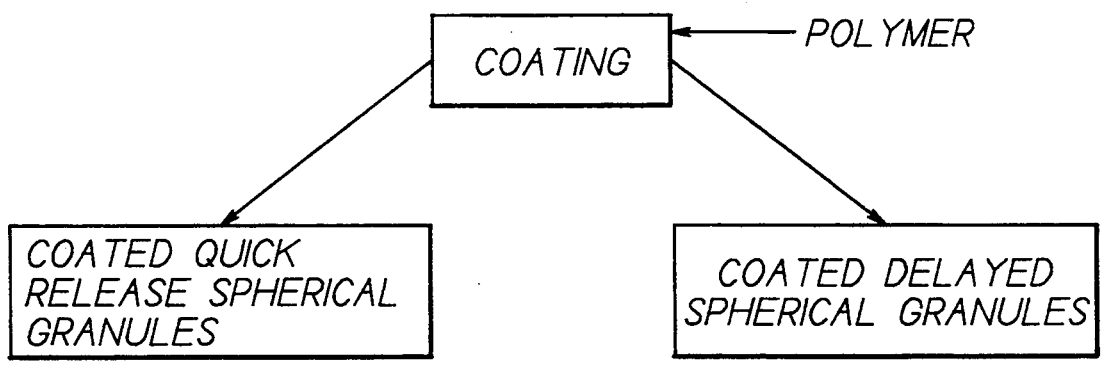
FIG. 2 is a graphic illustration of a method for the production of coated quick release granules and blended polymer coated spherical granules according to the present invention.

FIG. 2 illustrates that the quick release granules then, optionally, may be coated with a substantially uniform polymer coating which is rapidly and substantially completely erodible in a medium having a pH of less than about 3.9 with an aqueous or organic solvent, e.g. methylene chloride and/or methanol, solution of the desired coating forming polymer, using fluid bed technology, pan-coating or the like. Preferably, fluid beds are used. FIG. 2 also illustrates that the precursors of coated spherical granules are independently coated with a substantially uniform blended polymer coating which is rapidly and partially erodable in water and thereafter substantially completely erodible in a medium having a pH of from about 4.0 to about 7.5 in a manner as explained above.

An initial loading therapeutically effective number of uncoated quick release granules or, optionally coated quick release granules, may then be mixed in a low shear mixer with a secondary loading therapeutically effective number of blended polymer coated spherical granules.

A hard shell or a soft shell capsule may be at least partially filled and optionally sealed, as previously described, to form a capsule oral dosage unit form.

The pharmaceutical delivery systems, spheronized pharmaceutical compositions, or oral dosage unit forms containing them may be administered by ingestion, thereby maintaining a therapeutic minocycline level in the blood stream of a warm blooded mammal for about 24 hours, and thereby providing about a 24 hour therapeutic blood level from a once-a-day dosaging system.

DESCRIPTION OF THE PREFERRED EMBODIMENTS

The following examples illustrate the invention without limitation. All parts are given by weight unless otherwise indicated. Bioavailability is a function of, and is an absolute term that indicates measurement of, both the true rate and the total amount (extent) of drug that reaches the blood stream from an administered dosage form.

COMPARATIVE EXAMPLE 1A*

Figure 5:
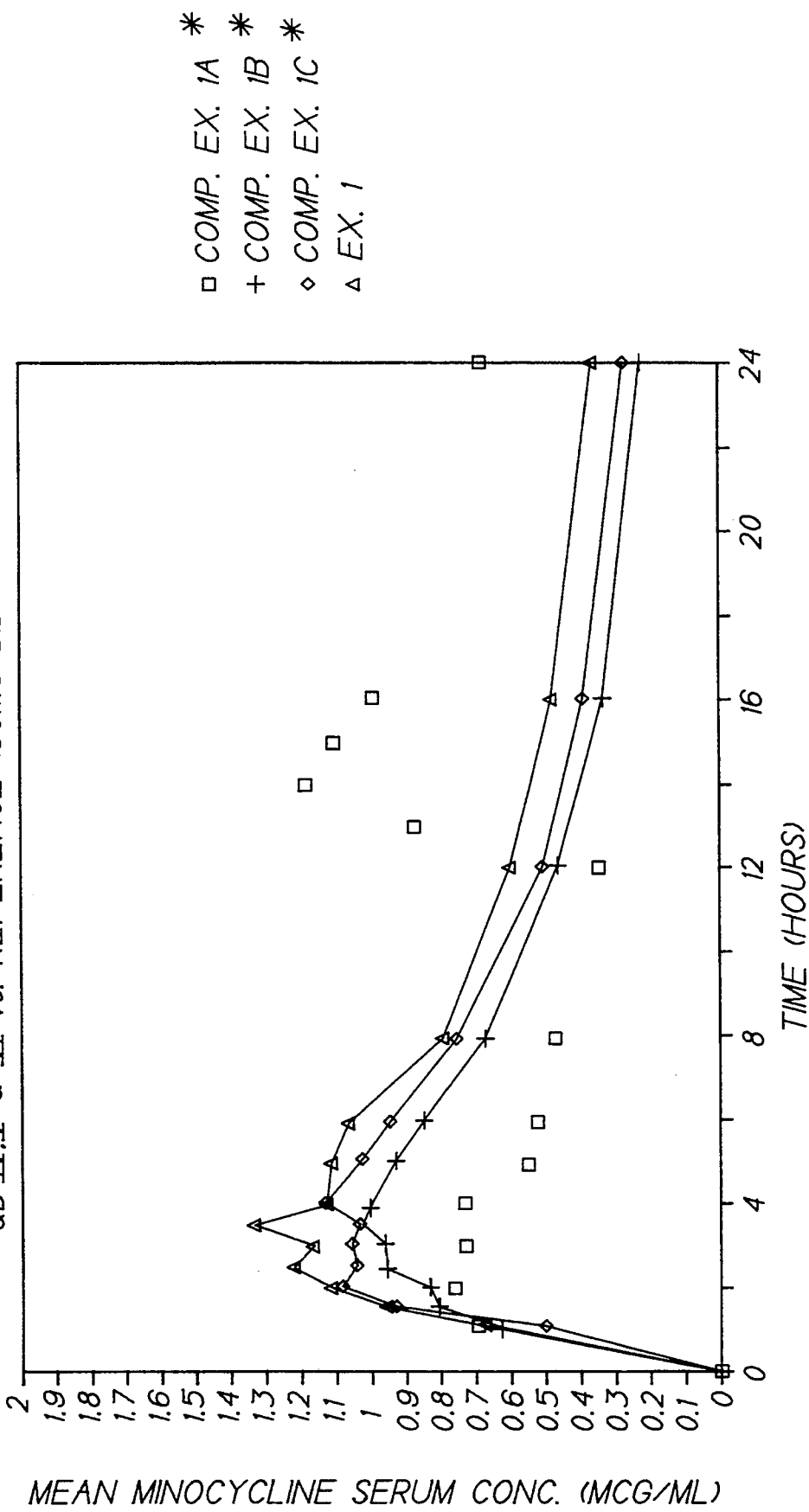
FIG. 5 is a graphic illustration of blood serum concentration levels of once-a-day administration of minocycline to human subjects in an oral dosage unit forms according to the present invention, in two oral dosage unit forms not according to this invention and a twice-a-day administration of minocycline in oral dosage unit form presently available from Lederle Laboratories.

One tablet containing 50 mg of minocycline hydrochloride (Minocin ®—Lederle Laboratories) is administered to a human subject, and serum concentration levels of minocycline hydrochloride are measured over a twelve hour period. A second tablet containing 50 mg of minocycline hydrochloride (Minocin ®) is administered to the subject at the end of the twelve hour period, and serum concentration levels of minocycline hydrochloride are measured over the next twelve hour period. The results appear in FIG. 5 in the curve identified as "Comparative Example 1A*".

Bioavailability is 100 percent because this is the reference for comparison.

A maximum serum concentration of minocycline hydrochloride during the first twelve hour period of 0.8 mcg/ml of serum is reached after 2 hours, and a maximum serum concentration of minocycline hydrochloride during the second twelve hour period of 1.3 mcg/ml is reached 2 hours after the administration of the second tablet. Minocycline hydrochloride plasma level concentration fluctuates broadly as in FIG. 5 can result in undesirable side effects such as nausea and gastroirritability.

COMPARATIVE EXAMPLE 1B*[QDIV]

(a) A blend is prepared by mixing 2500 parts of minocycline hydrochloride powder (Minocin ®—Lederle Laboratories) and 2500 parts of microcrystalline cellulose (Avicel ® PH-101, FMC Corporation) in a Hobart mixer at low speed. The powder blend is then granulated to an extrudable consistency by adding 3000 parts by volume of water slowly and mixing. The resultant granulate is extruded at high speed through a 1.0 mm plate in a NICA extruder/spheronizer model S450, and subsequently is spheronized at high speed. The wet spheres are dried in an Aeromatic fluid bed dryer at 70° C. air input until the moisture content is about 1 to 7 percent to form yellow uncoated quick release granules having a smooth surface and a homogeneous tetracycline compound distribution.

(b) A blend is prepared by mixing 3000 parts of minocycline hydrochloride powder (Minocin ®—Lederle Laboratories), 1650 parts of microcrystalline cellulose (Avicel ® PH-101, FMC Corporation) and 350 parts of AC-DI-SOL (crosscarmellose sodium) in a Hobart mixer at low speed. The powder blend is then granulated to an extrudable consistency by adding 3000 parts by volume of water slowly and mixing. The resultant granulate is extruded at high speed through a 1.0 mm plate in a NICA extruder/spheronizer Model S450, and subsequently is spheronized at high speed. The wet spheres are dried in an Aeromatic fluid bed dryer at 70° C. air input until the moisture content is about 1 to 7 percent to form precursors of coated spherical granules.

The core pellets are coated with a solution containing a blend of hydroxypropyl methylcellulose phthalate (HPMCP 50), a pH dependent polymer which dissolves at pH 5 and above, and hydroxypropyl methylcellulose (HPMC), a water-soluble pore forming polymer, which dissolves at all pH conditions. Thus the coating polymer system (HPMCP 50:HPMC) developed provides a coated system where some drug will be released in the acid environment of the stomach (pH 1-3) and rapid release of the remaining drug in the upper small intestine (pH 4.5-6.5).

To achieve this, a polymer coating blend is prepared by mixing 10.0 parts of hydroxypropyl methylcellulose phthalate (HPMCP-50, Shin-Etsu Chemical, Tokyo, Japan), 2.5 parts of hydroxypropyl methyl cellulose, 2.5 parts of mineral oil, and 1.67 parts of orange colorant (Opaspray K-1-2562, Colorcon, Inc., West Point, Pa.) and dissolving the mixture in an organic solvent.

The blended polymer coating solution is sprayed onto 900 grams of dried precursors of coated spherical granules at an initial rate of 7 ml/min which is gradually increased to 9 ml/min in an Uni-Glatt Model 82/E fluid bed until a 20 parts by weight gain based upon the weight of the precursors of coated spherical granules is achieved. Input air is adjusted to 54° C. while output air is adjusted between 22° and 25° C.

pH sensitive blended polymer coated spherical granules having a polymer coating adapted to release some drug in the acid environment of the stomach (pH 1-3) and to erode rapidly and substantially completely to release the rest of the drug in the upper small intestine (pH 4.5-6.5) are formed.

(c) 750 parts of quick release granules prepared by the method of Step (a) and 750 parts of the blended polymer coated spherical granules prepared by the method of Step (b) are mixed in a low shear blender at low speed for 15 minutes to form a spheronized pharmaceutical composition mixture.

(d) The mixture prepared by the method of Step (c) is filled into hard shell gelatin capsules to form oral dosage unit forms having a total minocycline content of 100 mg, with 50 mg of minocycline contained in the quick release granules and 50 mg of the minocycline compound contained in the pH sensitive blended polymers coated spherical granules.

Dissolution profiles of the minocycline hydrochloride are determined by U.S.P. XXI test methods using buffered media having pH's of 4.0 and 6.0. The results appear in FIGS. 3 and 4, respectively, in graph form.

COMPARATIVE EXAMPLE 1C*[QDV]

The procedure of Example 1B* is repeated except that Step (b) is modified as follows:

(b) A pH sensitive polymer coating blend is prepared by mixing 5.94 parts of hydroxypropyl methylcellulose phthalate (HPMCP-50, Shin-Etsu Chemical, Tokyo, Japan), 0.31 parts of hydroxypropyl methyl cellulose, 1.25 parts of mineral oil, and 0.83 parts of orange colorant (Opaspray K-1-2562, Colorcon, Inc., West Point, Pa.) and dissolving the mixture in an organic solvent.

The blended polymer coating solution is sprayed onto 900 parts of dried precursors of coated spherical granules in accordance with Step (b) in Comparative Example 1B* until a 10 parts by weight gain based upon the weight of the precursors of coated spherical granules is achieved.

Blended polymer coated spherical granules having a polymer coating adapted to release some drug in the acid environment of the stomach (pH 1–3) and to erode rapidly and substantially completely to release the rest of the drug in the upper small intestine (pH 4.5–6.5) are formed.

(c) 750 parts of quick release granules prepared by the method of Step (a) and 750 parts of the blended polymer coated spherical granules prepared by the method of Step (b) are mixed in a low shear blender at low speed for 15 minutes to form a spheronized pharmaceutical composition mixture.

(d) The mixture prepared by the method of Step (c) is filled into hard shell gelatin capsules to form oral dosage unit forms having a total minocycline content of 100 mg, with 50 mg of minocycline contained in the quick release granules and 50 mg of the minocycline compound contained in the pH sensitive blended polymers coated spherical granules.

Dissolution profiles of the minocycline hydrochloride are determined by U.S.P. XXI test methods using buffered media having pH's of 4.0 and 6.0. The results appear in FIGS. 3 and 4, respectively, in graph form.

EXAMPLE 1 [QDVI]

The procedure of Example 1C* is repeated except that Steps (b) and (c) are modified as follows:

(b) A polymer coating blend is prepared by mixing 8.0 parts of hydroxypropyl methylcellulose phthalate (HPMCP-50, Shin-Etsu Chemical, Tokyo, Japan), 2.0 parts of hydroxypropyl methyl cellulose, 2.0 parts of mineral oil, and 1.30 parts of orange colorant (Opaspray K-1-2562, Colorcon, Inc., West Point, Pa.) and dissolving the mixture in an organic solvent.

The blended polymer coating solution is sprayed onto 900 parts of dried precursors of coated spherical granules in accordance with Step (b) in Comparative Example 1C* until a 20 parts by weight gain based upon the weight of the precursors of coated spherical granules is achieved.

pH sensitive blended polymer coated spherical granules having a polymer coating adapted to release some drug in the acid environment of the stomach (pH 1–3) and to erode rapidly and substantially completely to release the rest of the drug in the upper small intestine (pH 4.5–6.5) are formed.

(c) 900 parts of quick release granules prepared by the method of Step (a) and 600 parts of the pH sensitive blended polymer coated spherical granules prepared by the method of Step (b) are mixed in a low shear blender at low speed for 15 minutes to form a spheronized pharmaceutical composition mixture.

(d) The mixture prepared by the method of Step (c) is filled into hard shell gelatin capsules to form oral dosage unit forms having a total minocycline content of 100 mg, with 60 mg of minocycline contained in the quick release granules and 40 mg of the minocycline compound contained in the pH sensitive blended polymers coated spherical granules.

Dissolution profiles of the minocycline hydrochloride are determined by U.S.P. XXI test methods using buffered media having pH's of 4.0 and 6.0. The results appear in FIGS. 3 and 4, respectively in graph form.

The dosage forms prepared above were formulated to determine the effect of several factors for improving bioavailability. These are described below:

1. Increase the uncoated portion of pellets in the formulation.
2. Incorporate pore creating agents in the polymer coating. e.g. coat the pellets with a blend of water soluble and pH sensitive polymer (HPMC/HPMCP 50) and vary the ratio of these two polymers.
3. Adjust the coating levels on pellets.

It is preferred to utilize Variable 2 to increase the bioavailability of the product since Variable 1 would potentially provide a product similar to immediate release product and Variable 3 might provide a product with greater variability in drug release, because of low coating level applied.

Each of the Comparative Examples 1B*, 1C* and Example 1 were developed utilizing all of the above variables. They were developed in 100 mg dosage strength. All of them contained a blend of yellow uncoated and orange coated pellets. They differed in their dissolution profiles when tested in pH 4.0 dissolution medium (Table 1 and FIG. 3). In pH 6.0 dissolution medium, all showed similar profiles, as expected, indicating complete release of drug occurred at pH 6.0 environment (Table 1 and FIG. 4).

The yellow uncoated quick-release pellets used in all of the Examples consisted of minocycline HCl and microcrystalline cellulose. The microcrystalline cellulose provides matrix controlled minocycline dissolution from these pellets. The core composition of the orange coated pellets used in all of the Examples includes minocycline HCl, microcrystalline cellulose and crosscarmellose sodium. The crosscarmellose sodium is included in the cores of the coated pellets to act as a disintegrant, thereby providing rapid break up of the cellulosic matrix for immediate release of drug following dissolution of coating polymer.

The core pellets are coated with a solution containing a blend of hydroxypropyl methylcellulose phthalate (HPMCP 50), a pH dependent polymer which dissolves at pH 5 and above, and hydroxypropyl methylcellulose (HPMC), a water-soluble pore forming polymer, which dissolves at all pH conditions. Thus the coating polymer system (HPMCP 50:HPMC) of the Examples provides a coated system where some drug will be released in the acid environment of the stomach (pH 1–3) and rapid release of the remaining drug in the upper small intestine (pH 4.5–6.5).

Considering the double pulse delivery design for these prototypes, the dissolution test method in two buffered media (pH 4.0 and pH 6.0) set for the above is appropriate because the pH 4.0 (0–02M Acetate Buffer) dissolution medium differentiates the dissolution profiles of these dosage forms as shown in FIG. 3. While the pH 6.0 (0.05M Phosphate Buffer) dissolution medium provides assurance of complete dissolution of minocycline in the upper part of the small intestine pH, as shown in FIG. 4.

These prototypes (QD-IV, QD-V & QD-VI; 100 mg capsules) were evaluated in humans against MINOCIN® tablets (50 mg BID), as reference, at Guy's Hospital in London in a pilot Bioavailability (BA) study. The pilot BA study screened the prototypes in a single dose study design.

The pilot study indicated that QD-VI showed 89% bioavailability, better than QD-IV (65%) or QD-V (80%) compared to reference. The results of this study are tabulated in Table 2 and graphically shown in FIG. 5. The QD-VI prototype was then selected for a multi-dose bioavailability study. The multi-dose study results are reported in Table 3.

TABLE 1

Minocycline QD IV, V and VI, Dissolution Data in pH 4.0 and pH 6.0 Buffer Media

| Time Minutes | % Minocycline dissolved (Mean ± SD, N = 12) | | |
|---|---|---|---|
| | QD-IV | QD-V | QD-VI |
| pH 4.0 Buffer | | | |
| 0 | 0 | 0 | 0 |
| 30 | 39.5 +/− 10.3 | 45.8 +/− 4.9 | 57.7 +/− 4.1 |
| 60 | 53.2 +/− 12.0 | 60.0 +/− 6.3 | 73.9 +/− 5.5 |
| 90 | 65.5 +/− 11.7 | 79.1 +/− 6.8 | 83.2 +/− 5.2 |
| 120 | 78.2 +/− 10.4 | 89.5 +/− 4.6 | 90.5 +/− 5.0 |
| pH 6.0 Buffer | | | |
| 0 | 0 | 0 | 0 |
| 30 | 74.3 +/− 6.3 | 80.3 +/− 3.2 | 76.7 +/− 5.9 |
| 60 | 95.8 +/− 5.9 | 102.4 +/− 2.7 | 96.6 +/− 5.1 |
| 90 | 99.9 +/− 5.2 | 104.2 +/− 2.3 | 103.3 +/− 2.3 |
| 120 | 102.3 +/− 4.2 | 104.5 +/− 2.4 | 105.4 +/− 1.8 |

TABLE 2

IN VIVO SUMMARY RESULTS ON QD-IV, QD-V & QD-VI PROTOTYPES
(100 mg Capsules)
Single Dose Study Data

| | Tmax (hrs.) | Cmax (mcg/ml) | Bioavailability AUC (4) (%) |
|---|---|---|---|
| MINOCIN ® Tablets (50 mg, BID) | 2.0 (14.3)* | 0.9 (1.3)* | 100 |
| QD-IV (100 mg, QD) | 2.8 | 1.2 | 62 |
| QD-V (100 mg, QD) | 3.1 | 1.3 | 80 |
| QD-VI (100 mg, QD) | 2.7 | 1.5 | 89 |

Number in ( ) is second dose data.

TABLE 3

MINOCYCLINE QD-6 MULTIDOSE DATA SUMMARY TABLE
DAY-6 (FAST) vs. DAY-7 (FED) DATA COMPARISON

| | MINOCIN TABLETS (50 mg, BID) | | QD-6 (100 mg CAPSULES) | |
|---|---|---|---|---|
| | DAY-6, FAST | DAY-7, FED | DAY-6, FAST | DAY-7, FED |
| Cmax (mcg/ml) | 1.88 (0.29)** | 1.79 (0.29) | 1.89 (0.48) | 2.00 (0.32) |
| Tmax (hrs.) | 1.60 (0.66) | 1.96 (1.00) | 2.56 (1.11) | 4.58 (1.64) |
| AUC (mcg · hr/ml) | 30.83 (5.68) | 27.90 (5.37) | 26.07 (7.01) | 26.12 (5.24) |
| Relative Bioavailability | | | | |
| QD-6/Ref. (Fasting)* | — | — | 84.6 | — |
| QD-6/Ref. (Fed)* | — | — | — | 93.6 |
| % Bioavailability | | | | |
| Effect of Food Fed/Fast | — | 90.6 | — | 100.08 |

*Percent relative bioavailability of QD-VI against reference, calculated by $\frac{AUC\ (QD\text{-}VI)}{AUC\ (Ref)} \times 100$

**Data in parenthesis is SD.

Examples 1B*, 1C* and 1 (FIGS. 3 and 4) demonstrate the selective release properties of blended polymer coated release spherical granules.

Example 1 demonstrates the ability of compositions and oral dosage unit forms of the present invention to maintain superior prolonged and controlled release of minocycline and thus the ability to provide a relatively even, at least minimum therapeutic blood concentration level of minocycline for up to about 24 hours with only once-a-day administration.

Comparative Example 1A* illustrates the uneven release rate and the broad fluctuations in blood levels of minocycline that result from conventional minocycline dosages.

Example 1 further demonstrates that the prolonged controlled release properties are also maintained in a fasting patient, thereby obviating the need for a patient to eat regularly for a therapeutic effect.

Comparative Example 1A* illustrates, when compared with Example 1, that the relatively low dosages of the present invention provide relatively even therapeutically effective concentration levels of minocycline.

Examples 1 in comparison with Comparative Examples 1B* and 1C* demonstrate that if the quick release pellets predominate, the oral dosage unit forms of the present invention are more bioavailable and less subject to reduction of bioavailability after eating.

All patents, applications, publications and test methods mentioned above are hereby incorporated by reference.

Many variations of the present invention will suggest themselves to those skilled in the art in light of the above detailed description. For example, the separate administration units can be different oral dosage unit forms including medicament-coated pellets and the ratio of quick release to slow release pellets can be as high as 80:20 parts by weight. All such modifications are within the full intended scope of the appended claims.

We claim:

1. An improved pharmaceutical delivery system adapted to provide a therapeutically effective blood concentration level of 7-dimethylamino-6-deoxy-6-demethyltetracycline or a non-toxic acid addition salt thereof for a sustained period of time of up to about twenty-four hours comprising:

(A) from 51 to 80 parts by weight per 100 parts by weight of (A) and (B) combined of an initial loading therapeutically effective number of quick release granules which comprise
  (a) (i) an effective amount of at least one pharmaceutically acceptable excipient; and
  (ii) an effective antibacterial amount of 7-dimethylamino-6-deoxy-6-demethyltetracycline or a non-toxic acid addition salt thereof, on or in said quick release granules;

said quick release granules being adapted to release substantially completely said tetracycline or salt thereof in a medium having a pH of less than about 3.9; and (B) from 20 to 49 parts by weight per 100 parts by weight of (A) and (B) combined of a secondary loading therapeutically effective number of blended polymer coated spherical granules which comprise
- (a) (i) an independent effective amount of at least one pharmaceutically acceptable excipient which may be the same as or different than (A)-(a)(i); and
  - (ii) an independent effective antibacterial amount of 7-dimethylamino-6-deoxy-6-demethyltetracycline or a non-toxic acid addition salt thereof, on or in said coated spherical granules; and
- (b) a substantially uniform pH sensitive coating comprising a blend of at least two polymers on said coated spherical granules (B) one of which is non pH-sensitive and rapidly erodible in water and the other of which is pH-sensitive and erodible in a medium having a pH in the range of from about 4.5 to about 6.5; said coated spherical granules thereby being adapted to release some of said tetracycline or salt thereof in a medium having a pH in the range of from about 1.0 to about 3.0 and the remainder rapidly in a medium having a pH in the range of from about 4.5 to about 6.5.

2. A pharmaceutical delivery system as defined in claim 1 wherein said quick release granules (A) comprise from about 55 to about 70 parts by weight and said coated granules (B) comprise from about 30 to about 45 parts by weight per 100 parts by weight of (A) and (B) together.

3. A pharmaceutical delivery system as defined in claim 2 wherein said quick release granules (A) comprise about 60 parts by weight and said coated granules (B) comprise about 40 parts by weight per 100 parts by weight of (A) and (B) together.

4. A pharmaceutical delivery system as defined in claim 1 wherein said tetracycline or salt thereof in said quick release granules comprises from about 10 to about 70 parts by weight and said at least one pharmaceutically acceptable excipient in said quick release granules comprises from about 90 to about 30 parts by weight based upon 100 parts by weight of said tetracycline or salt thereof and said excipient combined.

5. A pharmaceutical delivery system as defined in claim 4 wherein said tetracycline or salt thereof comprises about 50 parts by weight and said at least one pharmaceutically acceptable excipient comprises about 50 parts by weight based upon 100 parts by weight of said tetracycline or salt thereof and said excipient combined.

6. A pharmaceutical delivery system as defined in claim 1 wherein said minocycline in said coated spherical granules (B) comprises from about 10 to about 80 parts by weight and said at least one pharmaceutically acceptable excipient in said coated spherical granules comprises from about 90 to about 20 parts by weight based upon 100 parts by weight of said tetracycline or salt thereof and said excipient combined, and said blended polymer coating comprises from about 5 to about 35 parts by weight based upon 100 parts by weight of said tetracycline or salt thereof and said excipient combined.

7. A pharmaceutical delivery system as defined in claim 6 wherein said blended polymer coating comprises from about 5 to about 25 parts by weight based upon 100 parts by weight of said tetracycline or salt thereof and said excipient combined.

8. A pharmaceutical delivery system as defined in claim 7 wherein said tetracycline or salt thereof comprises about 60 parts by weight and said excipient comprises about 40 parts by weight based upon 100 parts of said minocycline and said excipient combined, and said blended polymer coating comprises from about 5 to about 25 parts by weight based upon 100 parts by weight of said tetracycline or salt thereof and said excipient combined.

9. A pharmaceutical delivery system as defined in claim 1 containing from about 25 to about 400 mg of 7-dimethylamino-6-deoxy-6-demethyltetracycline or a non-toxic acid addition salt thereof.

10. A pharmaceutical delivery system as defined in claim 9 containing about 80 to about 280 mg of 7-dimethylamino-6-deoxy-6-demethyltetracycline or a non-toxic acid addition salt thereof.

11. A pharmaceutical delivery system as defined in claim 1 wherein said initial loading (A) contains from about 20 to about 200 mg of 7-dimethylamino-6-deoxy-6-demethyltetracycline or a non-toxic acid addition salt thereof.

12. A pharmaceutical delivery system as defined in claim 1 wherein said blended polymer coated spherical granules (B) contain from about 20 to about 200 mg of 7-dimethylamino-6-deoxy-6-demethyltetracycline or a non-toxic acid addition salt thereof.

13. A pharmaceutical delivery system as defined in claim 1 wherein said excipient in said quick release granules (A) comprises lactose, other mono- or di-saccharides, microcrystalline cellulose, starch, sodium carboxymethyl cellulose, hydroxypropyl cellulose, hydroxyethyl cellulose, crosscarmellose sodium, pregelatinized starch, polyvinylpyrrolidone, cross-linked polyvinylpyrrolidone, hydroxypropylmethyl cellulose, cellulose acetate, hydroxypropyl methylcellulose phthalate, polyvinyl acetate phthalate, microcrystalline cellulose in combination with lactose, microcrystalline cellulose in combination with sodium carboxymethyl cellulose, microcrystalline cellulose in combination with crosscarmellose sodium, or a mixture of any of the foregoing.

14. A pharmaceutical delivery system as defined in claim 13 wherein said excipient in said quick release granules (A) comprises microcrystalline cellulose.

15. A pharmaceutical delivery system as defined in claim 13 wherein said excipient in said coated spherical granules (B) comprises microcrystalline cellulose in combination with crosscarmellose sodium.

16. A pharmaceutical delivery system as defined in claim 1 wherein said blended polymer coating blend comprises at least two polymers selected from
  (a) methylcellulose
  (b) ethylcellulose
  (c) hydroxyethyl cellulose
  (d) hydroxypropyl cellulose
  (e) hydroxypropyl methylcellulose
  (f) hydroxypropyl methylcellulose phthalate
  (g) cellulose acetate phthalate
  (h) hydroxypropyl methylcellulose succinate
  (i) a polymer or copolymer of (meth)acrylic acid or an ester thereof
  (j) polyvinyl acetate phthalate
  (k) a polymer or copolymer of polyvinyl acetate
  (l) cellulose acetate
  (m) fatty acids and esters thereof (n) cellulose acetate trimellitate; or (o) a mixture of any of the foregoing, alone, or in further combination with a plasticizer, a colorant, or a pigment; adapted to partially erode in water and to dissolve substantially completely in a medium having a pH in the range of from about 4.5 to about 6.5.

17. A pharmaceutical delivery system as defined in claim 16 wherein said blended polymer coating comprises hydroxypropyl methylcellulose phthalate adapted to dissolve substantially completely in a medium having a pH of from about 5.0 to about 5.5.

18. A pharmaceutical delivery system as defined in claim 16 wherein said blended polymer coating comprises a combination of hydroxypropyl methylcellulose phthalate and hydroxypropyl methylcellulose adapted to dissolve partially in water and substantially completely in a medium having a pH of above from about 5.0 to about 5.5.

19. A pharmaceutical delivery system as defined in claim 16 wherein said blended polymer coating comprises hydroxypropyl methylcellulose phthalate adapted to dissolve partially in water and substantially completely in a medium having a pH of greater than about 5.5.

20. A pharmaceutical delivery system as defined in claim 1 wherein said blended polymer coated spherical granules (B), said quick release granules (A), or both, independently, have an average diameter in the range of from about 0.1 to about 2.5 millimeters.

21. A pharmaceutical delivery system as defined in claim 20 wherein said blended polymer coated spherical granules (B), said quick release granules (A), or both, independently, have an average diameter in the range of from about 0.8 to about 1.2 millimeters.

22. A control led release pharmaceutical composition in oral dosage unit form comprising a hard or a soft shell capsule at least partially filled with a pharmaceutical delivery system as defined in claim 1.

23. An oral dosage unit as defined in claim 22 which also includes a lubricant, a disintegrant, a plasticizer, a colorant, a pigment, a flavoring, an additional medicament, or a combination of any of the foregoing.

24. A method of maintaining a therapeutically effective level of 7-dimethylamino-6-deoxy-6-demethyltetracycline or a non-toxic acid addition salt thereof in the blood stream of a warm-blooded mammal for about 24 hours comprising administering to said mammal a pharmaceutical delivery system as defined in claim 1.

* * * * *